(12) United States Patent
Shimmick et al.

(10) Patent No.: US 6,755,818 B2
(45) Date of Patent: *Jun. 29, 2004

(54) METHOD AND SYSTEM FOR LASER TREATMENT OF REFRACTIVE ERRORS USING OFFSET IMAGING

(75) Inventors: John K. Shimmick, Redwood City, CA (US); William B. Telfair, San Jose, CA (US); Charles R. Munnerlyn, Sunnyvale, CA (US); Herrmann J. Glockler, Cupertino, CA (US)

(73) Assignee: VISX, Incorporated, Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/730,072

(22) Filed: Dec. 5, 2000

(65) Prior Publication Data

US 2001/0000530 A1 Apr. 26, 2001

Related U.S. Application Data

(63) Continuation of application No. 08/968,380, filed on Nov. 12, 1997, now Pat. No. 6,203,539, which is a continuation of application No. 08/058,599, filed on May 7, 1993, now abandoned.

(51) Int. Cl.[7] .................................................. A61F 9/007
(52) U.S. Cl. .............................. 606/5; 606/10; 606/11; 606/13; 606/17; 606/18; 128/898
(58) Field of Search ........................... 606/2–6, 10–18; 128/848

(56) References Cited

U.S. PATENT DOCUMENTS

| | | |
|---|---|---|
| 4,461,294 A | 7/1984 | Baron |
| 4,665,913 A | 5/1987 | L'Esperance, Jr. |
| 4,669,466 A | 6/1987 | L'Esperance |

(List continued on next page.)

FOREIGN PATENT DOCUMENTS

| | | | |
|---|---|---|---|
| DE | 42 32 915 | 4/1994 | |
| EP | 280414 | * 1/1988 | .................. 606/10 |
| EP | 0 296 982 | 12/1988 | |
| EP | 0529822 | 3/1993 | |
| FR | 2633826 | 1/1990 | |

(List continued on next page.)

OTHER PUBLICATIONS

Hanna et al, "Excimer Laser Keratectomy for Myopia With a Rotating Slit Deivery System"; Arch. Ophthalmol.; Feb. 1988; pp 245–250.*

(List continued on next page.)

*Primary Examiner*—David M. Shay
(74) *Attorney, Agent, or Firm*—Townsend and Townsend and Crew LLP; Lynn Thompson

(57) ABSTRACT

An ophthalmological surgery system and method for performing ablative photodecomposition of the corneal surface by offset image scanning. The image of a variable aperture, such as a variable width slit and variable diameter iris diaphragm, is scanned in a preselected pattern to perform ablative sculpting of predetermined portions of a corneal surface. The scanning is performed with a movable image offset displacement mechanism capable of effecting radial displacement and angular rotation of the profiled beam exiting from the variable aperture. The profiled beam is rotated by rotating the aperture in conjunction with the offset displacement mechanism. The invention enables wide area treatment with a laser having a narrower beam, and can be used in the treatment of many different conditions, such as hyperopia, hyperopic astigmatism, irregular refractive aberrations, post ablation smoothing and photo therapeutic keratectomy.

21 Claims, 4 Drawing Sheets

U.S. PATENT DOCUMENTS

| | | |
|---|---|---|
| 4,718,418 A | 1/1988 | L'Esperance, Jr. |
| 4,729,372 A | 3/1988 | L'Esperance, Jr. |
| 4,732,148 A | 3/1988 | L'Esperance, Jr. |
| 4,770,172 A | 9/1988 | L'Esperance, Jr. |
| 4,773,414 A | 9/1988 | L'Esperance, Jr. |
| 4,798,204 A | 1/1989 | L'Esperance, Jr. |
| 4,840,175 A | 6/1989 | Peyman |
| 4,901,718 A | 2/1990 | Bille et al. |
| 4,903,695 A | 2/1990 | Warner et al. |
| 4,907,586 A | 3/1990 | Bille et al. |
| 4,911,711 A | 3/1990 | Telfair et al. |
| 4,973,330 A | 11/1990 | Azema et al. |
| 5,074,859 A | 12/1991 | Koziol |
| 5,090,798 A | 2/1992 | Kohayakawa |
| 5,163,934 A | 11/1992 | Munnerlyn |
| 5,219,344 A * | 6/1993 | Yoder, Jr. ............ 606/10 |
| 5,284,477 A * | 2/1994 | Hanna et al. ............ 606/10 |
| 5,309,186 A | 5/1994 | Mizuno |
| 5,342,351 A | 8/1994 | Blaha et al. |
| 5,355,253 A | 10/1994 | Nanjo et al. |
| 5,445,633 A | 8/1995 | Nakamura et al. |
| 5,470,329 A | 11/1995 | Sumiya |
| 5,500,697 A | 3/1996 | Fujieda |
| 5,507,799 A | 4/1996 | Sumiya |
| 5,624,436 A | 4/1997 | Nakamura et al. |
| 5,637,109 A | 6/1997 | Sumiya |
| 5,643,249 A | 7/1997 | Amano |
| 5,683,379 A | 11/1997 | Hohla |
| 6,203,539 B1 * | 3/2001 | Shimmick et al. ............ 606/11 |
| 6,319,247 B1 * | 11/2001 | Hofer et al. ............ 606/5 |

FOREIGN PATENT DOCUMENTS

| | | |
|---|---|---|
| GB | 2221162 | 1/1990 |
| WO | WO 91/08723 | 6/1991 |
| WO | WO 91/11158 | 8/1991 |
| WO | WO 92/13507 | 8/1992 |
| WO | WO 93/08877 | 5/1993 |
| WO | WO 93/14430 | 7/1993 |

OTHER PUBLICATIONS

W.J. Stark et al., "Clinical Follow–up of 193–nm ArF Excimer Laser Photokeratectomy", Ophthalmology, vol. 99, No. 5, May 1992, pp. 805–812.

N.A. Sher, et al., "Clinical Use of the 193–nm Excimer Laser in the Treatment of Corneal Scars", Arch. Ophthalmol., vol. 109, Apr. 1991, pp. 491–498.

Munnerlyn et al., "Photoreactive keratectomy: A technique for laser refractive surgery" *J. Cataract Refract. Surg.* (1988) 14:46–52.

* cited by examiner

METHOD AND SYSTEM FOR LASER TREATMENT OF REFRACTIVE ERRORS USING OFFSET IMAGING

CROSS-REFERENCES TO RELATED APPLICATIONS

This application is a continuation of, and claims priority from, U.S. patent application Ser. No. 08/968,380, filed Nov. 12, 1997, now U.S. Pat. No. 6,208,539 which is a continuation of U.S. patent application Ser. No. 08/058,599, filed May 7, 1993, now abandoned, the full disclosures of which are incorporated herein by referenced in their entirety.

BACKGROUND OF THE INVENTION

This invention relates to ophthalmological surgery techniques which employ a laser to effect ablative photodecomposition of the anterior surface of the cornea in order to correct vision defects.

Ultraviolet laser based systems and methods are known for enabling ophthalmological surgery on the surface of the cornea in order to correct vision defects by the technique known as ablative photodecomposition. In such systems and methods, the irradiated flux density and exposure time of the cornea to the ultraviolet laser radiation are so controlled as to provide a surface sculpting of the cornea to achieve a desired ultimate surface change in the cornea, all in order to correct an optical defect. Such systems and methods are disclosed in the following U.S. patents and patent applications, the disclosures of which are hereby incorporated by reference: U.S. Pat. No. 4,665,913 issued May 19, 1987 for "METHOD FOR OPHTHALMOLOGICAL SURGERY"; U.S. Pat. No. 4,669,466 issued Jun. 2, 1987 for "METHOD AND APPARATUS FOR ANALYSIS AND CORRECTION OF ABNORMAL REFRACTIVE ERRORS OF THE EYE"; U.S. Pat. No. 4,732,148 issued Mar. 22, 1988 for "METHOD FOR PERFORMING OPHTHALMIC LASER SURGERY"; U.S. Pat. No. 4,770,172 issued Sep. 13, 1988 for "METHOD OF LASER-SCULPTURE OF THE OPTICALLY USED PORTION OF THE CORNEA"; U.S. Pat. No. 4,773,414 issued Sep. 27, 1988 for "METHOD OF LASER-SCULPTURE OF THE OPTICALLY USED PORTION OF THE CORNEA"; U.S. patent application Ser. No. 109,812 filed Oct. 16, 1987 for "LASER SURGERY METHOD AND APPARATUS"; and U.S. Pat. No. 5,163,934 issued Nov. 17, 1992 for "PHOTOREFRACTIVE KERATECTOMY".

In the above-cited U.S. Pat. No. 4,665,913 several different techniques are described which are designed to effect corrections for specific types of optical errors in the eye. For example, a myopic condition is corrected by laser sculpting the anterior corneal surface to reduce the curvature. In addition, an astigmatic condition, which is typically characterized by a cylindrical component of curvature departing from the otherwise generally spherical curvature of the surface of the cornea, is corrected by effecting cylindrical ablation about the axis of cylindrical curvature of the eye. Further, a hyperopic condition is corrected by laser sculpting the corneal surface to increase the curvature.

In a typical laser surgical procedure, the region of the anterior corneal surface to be ablated in order to effect the optical correction is designated the optical zone. Depending on the nature of the desired optical correction, this zone may or may not be centered on the center of the pupil or on the apex of the anterior corneal surface.

The technique for increasing the curvature of the corneal surface for hyperopia error correction involves selectively varying the area of the cornea exposed to the laser beam radiation to produce an essentially spherical surface profile of increased curvature. This selective variation of the irradiated area may be accomplished in a variety of ways. For example, U.S. Pat. No. 4,665,913 cited above discloses the technique of scanning the region of the corneal surface to be ablated with a laser beam having a relatively small cross-sectional area (compared to the optical zone to be ablated) in such a manner that the depth of penetration increases with distance from the intended center of ablation. This is achieved by scanning the beam more times over the deeper regions than the shallower regions. As pointed out in U.S. Pat. No. 5,163,934, such ablations tend to be rougher than area ablations. The result is a new substantially spherical profile for the anterior corneal surface with maximum depth of cut at the extreme outer boundary of the optical zone. Another technique disclosed in the above-cited U.S. Pat. No. 4,732,148 employs a rotatable mask having a plurality of elliptical annular apertures which are progressively inserted into the laser beam path to provide progressive shaping of the laser beam in order to achieve the desired profile.

One of the major difficulties encountered in the application of laser surgery techniques to effect hyperopic refractive error corrections lies in the nature of the boundary between the optical zone and the untreated area. Since the anterior surface of the cornea is sculpted during the process to have an increased curvature, the maximum depth of cut necessarily occurs at the outer boundary of the optical zone. The generally annular region between this outer boundary and the adjacent untreated anterior surface portion of the cornea typically exhibits steep walls after the completion of the photoablation procedure. After the surgery the tendency of the eye is to eliminate these steep walls by stimulated healing response involving concurrent epithelial cell growth and stromal remodelling by the deposition of collagen, which results in corneal smoothing by filling in tissue in the steep walled region. This natural healing response acts to eliminate the discontinuity, resulting in a buildup of tissue in the steep walled region and over the outer portion of the optical zone. This natural phenomenon, sometimes termed the "hyperopic shift" in phototherapeutic keratectomy, causes a lack of precision for a given surgical procedure and diminished predictability, which tend to counteract the beneficial effects of the refractive correction procedure and thereby reduce the desirability of the procedure to the prospective patient.

Efforts have been made in the past to laser sculpt a transition zone to provide a more gradual sloping of the walls and to eliminate the sharp discontinuity between the outer edge of the optical zone and the edge of the untreated area. Efforts have included the use of a beam rotation or scanning mechanism operated by a computer to provide programmed ablation of the transition zone to achieve a sigmoidal or other profile. While somewhat effective, these efforts suffer from the disadvantage of typically requiring additional optical elements (such as a rotatable off-axis mirror or revolving prism having suitable optical properties) which adds complexity to the delivery system optics commonly found in laser sculpting ophthalmological surgical systems. One specific technique, which is disclosed in published European Patent Application No. 0 296 982 published Dec. 28, 1988, employs a rotatable mask having one or more profiling apertures whose shape is designed to provide a smoother profile in the transition zone in the course of performing a specific ablation procedure. This reference also teaches the use of a rotating prism aligned along the beam axis in combination with a translatable platform bearing a focusing lens in order to both translate and rotate the aperture image along the anterior corneal surface. This technique, while considered effective for some purposes, requires a relatively complicated optical delivery system in order to provide the desired profiling. In addition, the use of mirrors and prisms in delivery system optics in laser surgery systems suffers from certain disadvantages. In particular, the addition of prisms decreases the total energy transmission of the system. Further, the reflectance of dielectric mirrors used in certain systems varies with reflectance angle, which can dynamically alter the irradiance delivered to the cornea while displacing the beam image over the cornea.

Another difficulty encountered in the application of laser surgery techniques to effect hyperopic refractive error corrections lies in the requirement for relatively large transition zones outside the optical zone. In particular, while the intended optical zone is typically on the order of about 5 mm in diameter, the outer limit of the transition zone can be as large as 10 mm in diameter. If the rotating mask arrangement described above is used to effect the ablation in both the optical zone and the transition zone, the beam diameter must be commensurate in size with the largest aperture outer diameter (i.e., at least about 10 mm). In general, the larger the beam diameter the less uniform the energy density across the beam and the less reliable the photoablation process. Further, the increased beam area requires a laser beam of substantially greater energy, which necessitates a more expensive laser. Also, the increased energy flowing through the optical components causes optical deterioration at a faster rate, thereby increasing maintenance and replacement costs. Another disadvantage inherent in a rotating mask system is that the resulting ablation frequently exhibits a central ablation surface which is rougher than desired when a hyperopic correction is conducted.

SUMMARY OF THE INVENTION

The invention comprises a method and system for performing ablative photodecomposition of the corneal surface which is capable of providing relatively smooth transition zones along with accurate sculpting of the anterior or other corneal surface to effect symmetric or asymmetric refractive corrections requiring relatively large area coverage. The invention is further capable of smoothing the corneal surface after a refractive correction has been ablated, and is further effective in performing phototherapeutic keratectomies. The invention uses a laser beam of smaller beam size than known devices, and can be readily designed into new ophthalmological surgery systems or retrofitted in existing ophthalmological surgery systems.

From a method standpoint, the invention comprises the steps of directing a laser beam toward a variable aperture, profiling the beam with the variable aperture to produce a variable area profiled beam, and scanning the profiled beam over a predetermined area of a corneal surface of an eye while varying the profile in a predetermined manner. The step of profiling can include the alternative steps of intercepting the laser beam with a variable width slit or a variable diameter diaphragm, or both; and the step of scanning may include the step of selectively varying the slit width, the diameter of the diaphragm, or both. During scanning, an axis of rotation for the profiled beam may be established and the profiled beam is radially displaced from the axis of rotation by a preselected amount during scanning. The angular position of the profiled beam about the axis of rotation may also be varied in a predetermined manner during scanning.

Various corrective procedures can be performed according to the method of the invention. In a first procedure, the scanning is performed by scanning the beam over successive arcuate or annular bands in the predetermined area of the corneal surface. In another procedure, the profiled beam is scanned over a predetermined portion of the area of the corneal surface while alternately enlarging and reducing the size of the variable aperture. The predetermined portion of the area may comprise a central zone of the corneal surface or an outer region of the corneal surface.

The step of scanning may be preceded by the steps of establishing an optical zone on the anterior corneal surface in which the desired refractive correction is to be effected, the optical zone having an outer boundary, and establishing a transition zone between the optical zone and the remaining anterior corneal surface. After establishing the optical zone and the transition zone, the scanning step is performed by scanning the profiled beam over the optical zone and the transition zone. The transition zone has an inner boundary and an outer boundary, and the step of profiling the beam may be conducted by intercepting the beam with a variable diameter diaphragm and a variable width slit having inner and outer edges, and the step of scanning is performed by maintaining that portion of the profiled beam corresponding to the intersection of the diaphragm and the outer edge of the slit adjacent the outer boundary of the transition zone. During scanning, the slit width can be narrowed by translating the inner edge of the slit toward the outer edge.

The step of scanning may be preceded by the steps of creating a treatment table containing a listing of coordinate references for the profiled beam and the number of laser pulses at each coordinate reference required to effect the desired refractive correction, and sorting the listings in the treatment table to establish a scanning pattern for the profiled beam.

From another method aspect, the invention includes the step of directing a laser beam along a path, profiling the beam with a variable aperture to produce a profiled beam, establishing an axis of rotation, displacing the profiled beam from the axis of rotation, and varying the angular position of the profiled beam about the axis of rotation to cause the beam to describe a path about a center of rotation corresponding to a desired ablation center. The step of profiling the beam may be performed by intercepting the laser beam with a variable aperture, such as a variable diameter width slit or a variable diameter iris diaphragm or both, and varying the aperture size in a predetermined manner while varying the displacement of the profiled beam in a manner related to the slit width. In a preferred implementation of the method, the steps of displacing the profiled beam and varying the angular position of the profiled beam are performed with an imaging lens by radially displacing the lens from the path and rotating the lens about the center of rotation.

To effect a predetermined hyperopic refractive correction, the method comprises the steps of directing a laser beam along a path, and selectively irradiating the corneal surface of the eye to ablate the appropriate contour required to effect the hyperopic refractive correction by intercepting the beam with a variable width slit to produce a profiled beam having an initial width, displacing the profiled beam exiting the slit by an initial amount from the axis of rotation, rotating the slit by a predetermined angular amount about the axis of rotation, adjusting the slit width, displacing and rotating the profiled beam exiting the slit by selected amounts, and repeating the steps of rotating the slit, adjusting the slit width and displacing and rotating the profiled beam until the hyperopic correction is completed. The step of displacing the profiled beam exiting the slit is preferably performed such that the edge portion of the exiting profiled beam associated to a first slit edge initially impinges the optical zone adjacent the center and the edge portion of the exiting beam associated to a second slit edge impinges the desired transition zone adjacent the outer edge. According to this method, the edge portion of the exiting profiled beam associated to the first slit edge impinges the optical zone at progressively increasing distances from the center and the edge portion of the exiting profiled beam associated to the second slit edge impinges the transition zone adjacent the outer edge. Preferably, the step of displacing and rotating the profiled beam by selected amounts is performed with an imaging lens positioned between the slit and the eye by first displacing and rotating the lens from a starting position, pulsing the laser and then rotating the lens to a subsequent angular position, which is preferably the existing position plus a predetermined incremental amount.

From an apparatus aspect, the invention comprises an ophthalmological surgery system for performing selective ablation of the corneal surface of an eye to effect a desired refractive correction, the system comprising means for directing a laser beam along a path, variable aperture means for profiling the beam to produce a variable area profiled beam, and means for scanning the profiled beam over a predetermined area of the corneal surface while varying the profile in a predetermined manner. The variable aperture profiling means preferably comprises a variable width slit and means for selectively varying the slit width during scanning. Alternatively, the variable aperture profiling means may comprise a variable diameter diaphragm, preferably an iris diaphragm, and means for selectively varying the diameter of the diaphragm during scanning. The scanning means includes means for radially displacing the profiled beam from an axis of rotation by a preselected amount, and means for varying the angular position of the profiled beam about an axis of rotation in a predetermined manner. The scanning means preferably includes an imaging lens positioned in the path of the profiled beam and means for displacing and rotating the lens means with reference to an axis of rotation. For the preferred embodiment in which the variable aperture profiling means includes a variable width slit and means for rotating the slit, the means for displacing and rotating the lens means and the means for rotating the slit are operationally coupled.

The system and method can be incorporated into existing laser surgery systems having a variable diameter iris aperture and a variable width slit mounted on a rotatable platform by modifying the mounting mechanism used for the existing imaging lens to enable the lens to be translated radially of an axis of rotation and rotated with the slit platform about the axis of rotation. The invention is capable of providing wider area beam coverage of the corneal surface with a laser having a conventional beam size, thereby eliminating any need for a larger beam laser and providing wider area coverage with lower energy requirements than many known devices.

For a fuller understanding of the nature and advantages of the invention, reference should be had to the ensuing detailed description taken in conjunction with the accompanying drawings.

DESCRIPTION OF THE SPECIFIC EMBODIMENTS

Figure 1:
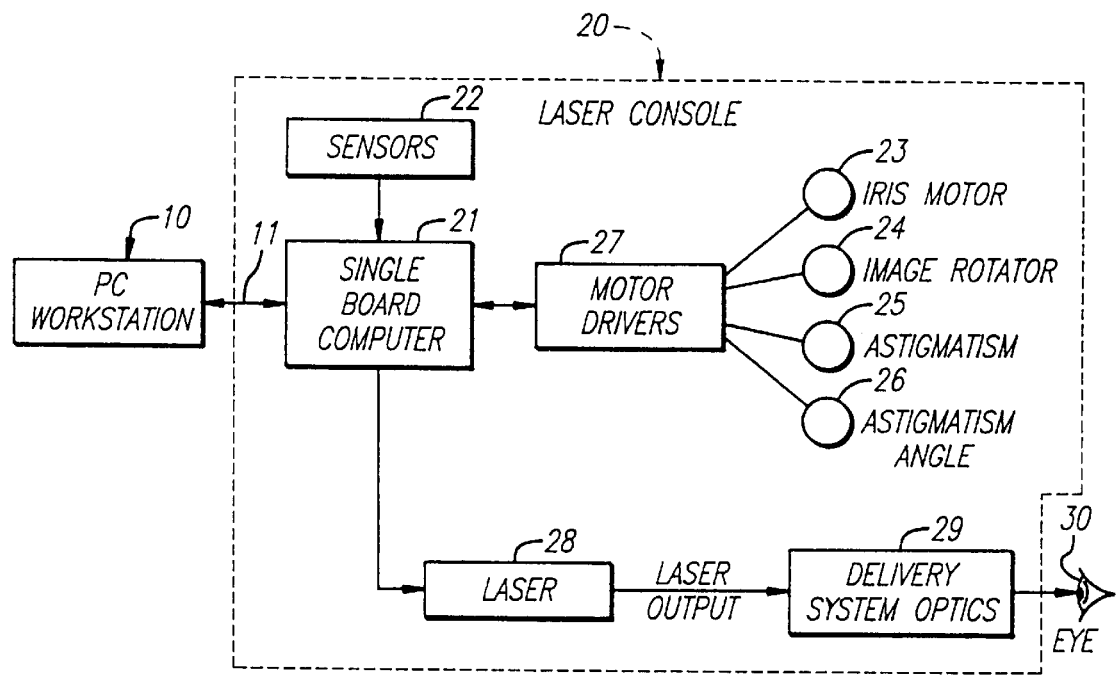
FIG. 1 is a block diagram of an ophthalmological surgery system for incorporating the invention.

Turning now to the drawings, FIG. 1 illustrates a block diagram of an ophthalmological surgery system for incorporating the invention. As seen in this Fig., a personal computer (PC) work station 10 is coupled to a single board computer 21 of a laser surgery unit 20 by means of a first bus connection 11. PC work station 10 and the subcomponents of laser surgery unit 20 are known components and preferably comprise the elements of the VISX TWENTY/TWENTY EXCIMER LASER SYSTEM available from Visx, Incorporated of Santa Clara, Calif. Thus, the laser surgery system 20 includes a plurality of sensors generally designated with reference numeral 22 which produce feedback signals from the movable mechanical and optical components in the laser optical system, such as the elements driven by an iris motor 23, an image rotator 24, an astigmatism motor 25 and an astigmatism angle motor 26. The feedback signals from sensors 22 are provided via appropriate signal conductors to the single board computer 21, which is preferably an STD bus compatible single board computer using a type 8031 microprocessor. The single board computer 21 controls the operation of the motor drivers generally designated with reference numeral 27 for operating the elements 23–26. In addition, single board computer 21 controls the operation of the Excimer laser 28, which is preferably an argon-fluorine laser with a 193 nanometer wavelength output designed to provide feedback stabilized fluence of 160 mjoules per $cm^2$ at the cornea of the patient's eye 30 via the delivery system optics generally designated with reference numeral 29 and shown in FIG. 6. Other ancillary components of the laser surgery system 20 which are not necessary to an understanding of the invention, such as a high resolution microscope, a video monitor for the microscope, a patient eye retention system, and an ablation effluent evacuator/filter, as well as the gas delivery system, have been omitted to avoid prolixity. Similarly, the keyboard, display, and conventional PC subsystem components (e.g., flexible and hard disk drives, memory boards and the like) have been omitted from the depiction of the PC work station 10.

Figure 2:
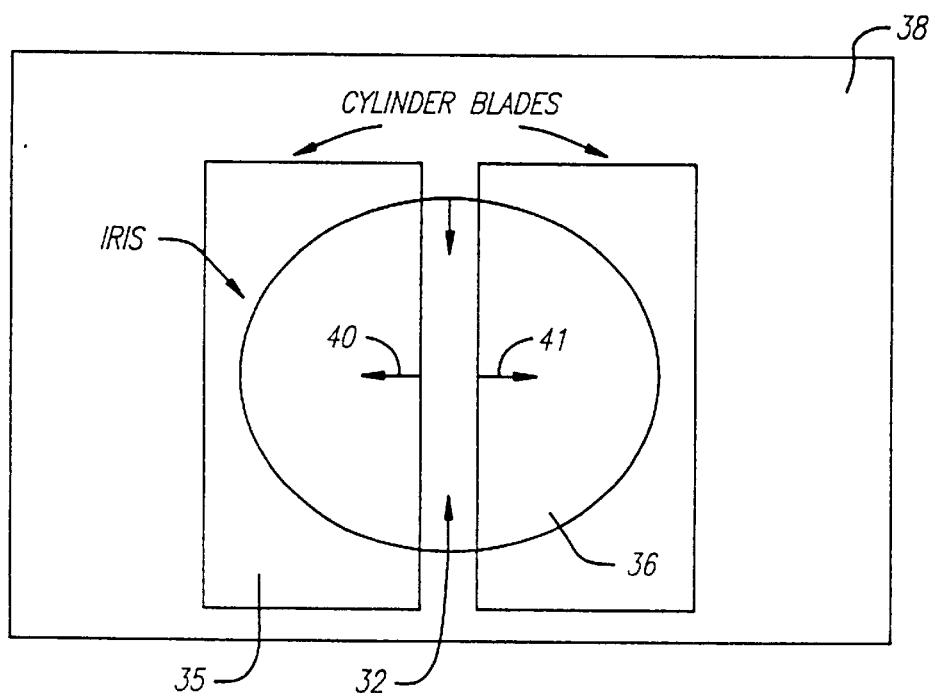
FIG. 2 is a schematic plan view illustrating a movable slit and variable diameter aperture used in the system of FIG. 1.

The iris motor 23 is used to control the diameter of a variable diameter iris schematically depicted in FIG. 2. The astigmatism motor 25 is used to control the separation distance between a pair of cylinder blades 35, 36 which are mounted on a platform 38 for bi-directional translatory motion in the direction of arrows 40, 41. Platform 38 is rotatably mounted on a second platform (not illustrated) and is rotationally driven by astigmatism angle motor 26 in a conventional way in order to enable alignment of the slit axis (illustrated in a vertical orientation in FIG. 2) with the appropriate coordinate axes of the patient's eye. Iris 32 is driven by iris motor 23 in a known way to change the diameter of the iris opening from a fully opened position (the position illustrated in FIG. 2) to a fully closed position in which the aperture is closed to a minimum diameter of 0.8 mm. It is understood that the variable diameter iris 32 and the cylinder blades 35, 36 are positioned with respect to the output of laser 28 in such a manner as to intercept the beam prior to irradiation of the corneal surface of the patient's eye 30. For the purpose of this application, it may be assumed that iris 32 and cylinder blades 35, 36 are part of the delivery system optics subunit 29 shown in FIG. 1.

Figure 3:
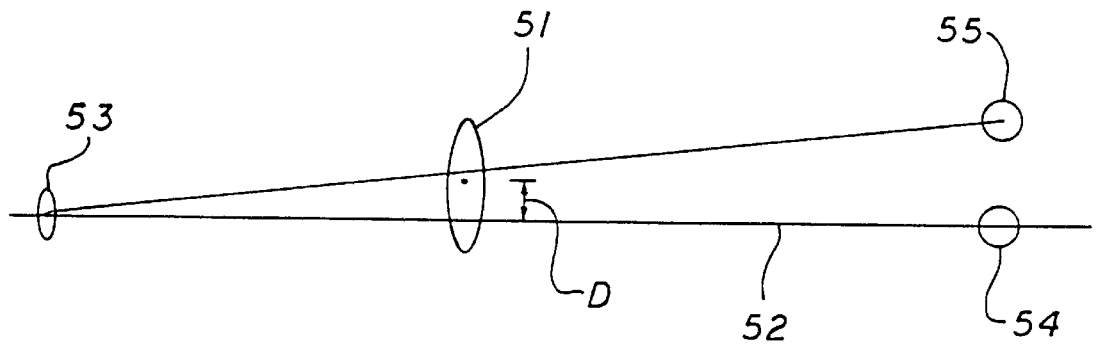
FIG. 3 is a schematic diagram illustrating the offset lens principle.
Figure 4:
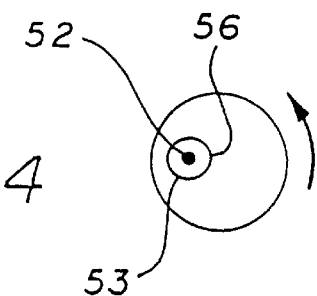
FIG. 4 is a schematic diagram illustrating the lens offset viewed along the axis of rotation.

The system of FIGS. 1 and 2 is used according to the invention to effect hyperopic and other error corrections to the anterior surface of the cornea, to provide a smooth transition zone between the outer edge of the optical zone and the untreated surface of the cornea, and to effect surface smoothing when desired. With reference to FIG. 3, an imaging lens 51 is laterally offset from an axis 52 by a variable amount in the manner set forth more fully below. Lens 51 preferably comprises the existing imaging lens found in the delivery system optics 29 of the FIG. 1 system which are described more fully below. Axis 52 is the axis corresponding to the center of rotation of lens 51. Displacing lens 51 by translating the lens in a radial direction off the axis 52, which may or may not correspond to the laser beam axis, displaces the image 54 of aperture 53 in a related manner. By also rotating lens 51 about the axis 52 in an eccentric fashion, as illustrated in FIG. 4, the displaced image 54 of aperture 53 can be scanned about axis 52 along a preselected path, which in the hyperopic correction procedure described below is an annular path about the axis 52. Depending upon the manner in which the slit width and iris diameter are controlled in combination with the off axis translation of lens 51 and eccentric rotation of lens 51 about axis 52, various types of large area ablation corrections can be effected, including hyperopic error corrections, hyperopic astigmatism corrections, and other vision error corrections, along with simultaneous or successive edge contouring to form a smooth transition zone.

Figure 5:
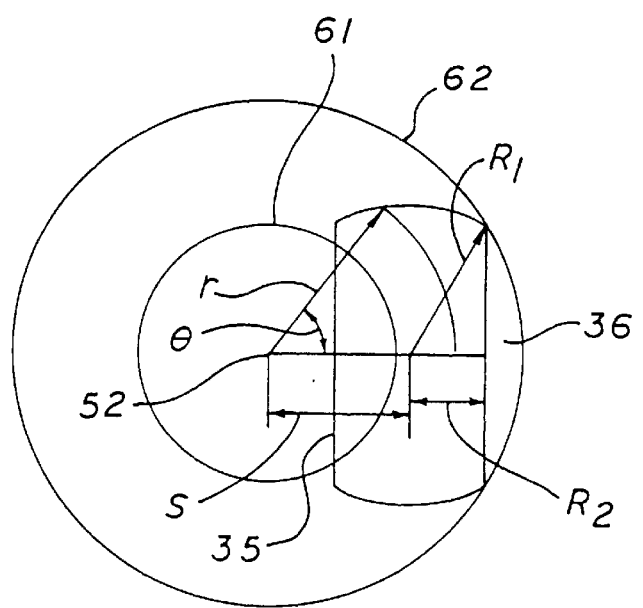
FIG. 5 is a schematic view showing the ablation geometry for the aperture of FIG. 2.

FIG. 5 illustrates the aperture positioning relative to the intended ablation center when employing the variable diameter iris 32 and cylinder blades 35, 36 of FIG. 2 to effect a refractive error correction. In this Figure, $R_2$ represents the half width of the slit between blades 35, 36, $R_1$ is the radius of the iris 32, r is the radius of a circle covered by the aperture, s is the radial offset of the center of the image of the slit aperture relative to the center of rotation 52, and è is the half angle for which the circle of radius r is covered by the aperture. The intended optical zone is the central region bounded by circle 61 and the intended transition zone is the annular region bounded by circles 61 and 62.

The manner in which the slit width and diameter are varied by the computer depends upon the type of vision correction desired. For a hyperopic dioptric correction of a given fixed value, the sequencing of the aperture is done in such a manner as to satisfy the hyperopic lens equations described in "Photorefractive Keratectomy: A technique for laser refractive surgery" authored by Munnerlyn et al., *J. Cataract Refract. Surg*. Vol. 14:46–52 (January 1988), the disclosure of which is hereby incorporated by reference.

A fixed value of the dioptric correction is used to generate the cut profile c(r). The cut profile is given by the equation:

$$i\ c(r) = (d/\pi)\Sigma(n_i \theta_i(r)) \tag{I}$$

where $n_i$ is the number of laser pulses for the $i_{th}$ aperture in a sequence of aperture dimensions and radial positions, and d is the amount of material removed with each laser pulse or a scaling factor which also takes into account corneal healing. The sequence of aperture dimensions is created by control of the width of the slit and the diameter of iris 32 throughout the surgical procedure. The sequence of aperture dimensions may also be tailored to accommodate variations in the profile of the laser beam.

For the example shown in FIG. 5, the values of s and $R_2$ are varied to produce the correct value of radial offset (s) and slit width ($2 \times R_2$) so that the inner edge of blade 35 is moved in steps from close to the center of the ablation (starting at approximately 0.6 mm from the center) to the edge of the corrected optical zone at approximately 2.5 mm. $R_1$ (the iris radius) is fixed at a predetermined value (3 mm in one specific procedure), and s and $R_2$ are chosen to anchor the edge of the ablation at the outer edge of the intended transition zone of approximately 5 mm radius. The number of pulses for each successive position of the inner edge is calculated to give the desired depth from the hyperopic lens equation. For a procedure requiring the least number of pulses, the treatment is ended as soon as the inner edge of the aperture reaches the boundary of the corrected optical zone. Initially, the slit width is set to a maximum value and the imaging lens 51 is positioned laterally of the axis of rotation 52 such that the inner slit edge is positioned at the minimum distance from the center of the optical zone and the intersections of the iris diaphragm 32 and the outer slit edge are positioned over the outer edge of the intended transition zone.

The image of the aperture is now ready to be scanned over the anterior surface of the cornea. While several different scanning sequences are possible, the following sequence has been actually implemented with effective results. The radial position along the optical zone is broken into a series of discrete, equidistant (typically 0.1 mm apart) nodes. The number of pulses required to ablate tissue to cut depth c(r) at a node adjacent to the edge of the inner slit is calculated using $$n = (\pi^* \sigma c(r_n))/(\theta_i(r_n)^* d) \tag{II}$$

where n is the number of pulses, σc(r) the difference between the actual ablation depth from previous pulses and the desired ablation depth at the node, $\theta_i(r_n)$ is the half angle coverage of the aperture at $r_n$ as previously defined. The radial ablation profile from previous pulses is calculated by summing the ablation depth from previous positions and pulses at each node as described by equation I. For the initial position, σc(r)=c(r). The number of pulses required for each subsequent node is calculated for each node adjacent to the inner cylinder blade as the blade moves toward the edge of the optical zone.

Having determined the correct number of pulses at each node, the treatment must be smoothed rotationally to ensure that it is correct and free from aberrations. Such smoothing is accomplished by rotating the treatment in FIG. 5 about axis 52. Typically, this rotation is about 127° between pulses. However, the stepper motors may take hundreds of seconds to drive the optomechanical parts into position, and the treatment is expedited by sorting the treatment table by angle on the workstation. However, if the treatment were to be interrupted, sorting the table by angle alone would cause the patient to be left with a pie shaped portion of optically correct cornea (pie in the eye). This can be avoided by breaking the treatment table into annular bands of 5 to 10 nodes each. The treatment table is then sorted by angle within each band. Should an interruption in the laser firing occur, the patient is left with a substantially radially symmetric partially complete sculpting. Such an ablation is much easier to realign for completion of the surgery.

The treatment bands may be further subdivided to form hemi-annular regions. This may be advantageous when the aperture can not be rotated by a full 360°, and the eccentric lens motion should be minimized. In such case, the first half of a treatment band is ablated, the aperture left in similar angular position, the imaging lens 51 is rotated 180°, and the other half of the band is ablated with subsequent pulses. Upon completion of the second half of the band, the aperture is left in nearly the same rotational position as it was for the start of the first half of the band, and is consequently well positioned for the start of the second band. Such motion will keep the range of rotation of the aperture under 180°, which is particularly advantageous in systems which are retrofitted and may have been designed only for the treatment of astigmatism.

To further expedite the surgery, the cylinder blades can be left at constant width during each band by closing the cylinder blades so that at the outermost node of the band, the intersection of the iris diaphragm and outer cylinder blade is coincident with the outer boundary of the ablation. The steps of rotating the treatment and sorting it within bands can all be performed on the workstation prior to treating the patient.

The laser 28 is pulsed, and platform 38 and lens 51 are rotated to a successive angular position displaced from the previous position by an angular amount determined by a treatment table described below. In addition, any required radial re-positioning of lens 51 may be done at this time. The laser is again pulsed, platform 38 and lens 51 are again rotated, the laser is again pulsed, etc. This process continues until all 360° have been covered in incremental steps. Next, the slit width is adjusted by narrowing the width by a predetermined amount, and the lens 51 is adjusted to place the inner slit edge at the appropriate radial position. Thereafter, another series of rotations of platform 38 and lens 51 is carried out, after which the slit width and the radial offset position of lens 51 are adjusted until the inner edge of the slit has reached the boundary 61 of the optical zone and the final series of angular positions has been carried out.

The above scanning procedure can be improved by rotating the imaging lens 51 by 180° between laser pulses, followed by the incremental shifting by a predetermined angular amount. Alternatively, lens 51 can be simply translated diametrically across the axis of rotation. This large angle displacement ensures that diametrically opposite portions of the anterior corneal surface are successively exposed to the profiled laser beam with no overlapping between pulses, which minimizes tissue heating.

Figure 6:
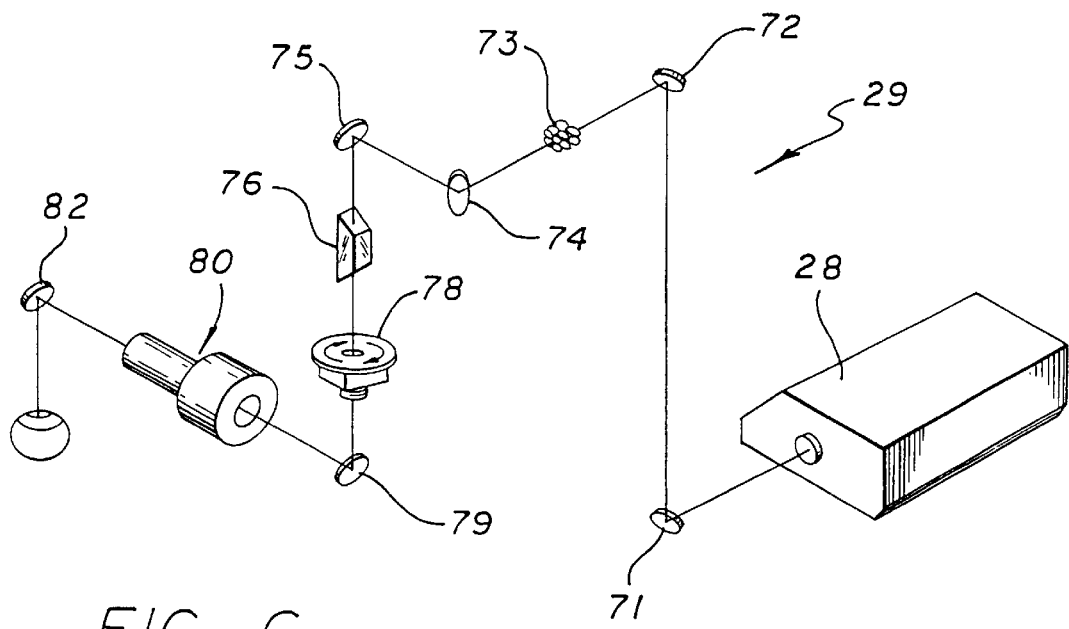
FIG. 6 is a schematic view of the delivery system optics.

FIG. 6 is a schematic view of the delivery system optics in the preferred embodiment. As seen in this Fig. the beam from laser 28 is reflected by a first mirror 71 and a second mirror 72, and enters a spatial integrator 73, where the beam is modified in cross-section. The modified beam exiting from spatial integrator 73 is reflected by mirrors 74 and 75 and passed through a dove prism 76 to the iris/slit mechanism 78 which contains the variable width slit and variable diameter iris described above. The profiled beam exiting from the unit 78 is reflected by a mirror 79 and enters the image offset control unit 80 which contains imaging lens 51. The offset profiled image exiting from unit 80 is reflected from a mirror 82 onto the patient's eye. To smooth out fluctuations in beam energy across the beam area, dove prism 76 is rotatably mounted, and is typically rotated during beam generation either continuously or between pulses.

Figure 7:
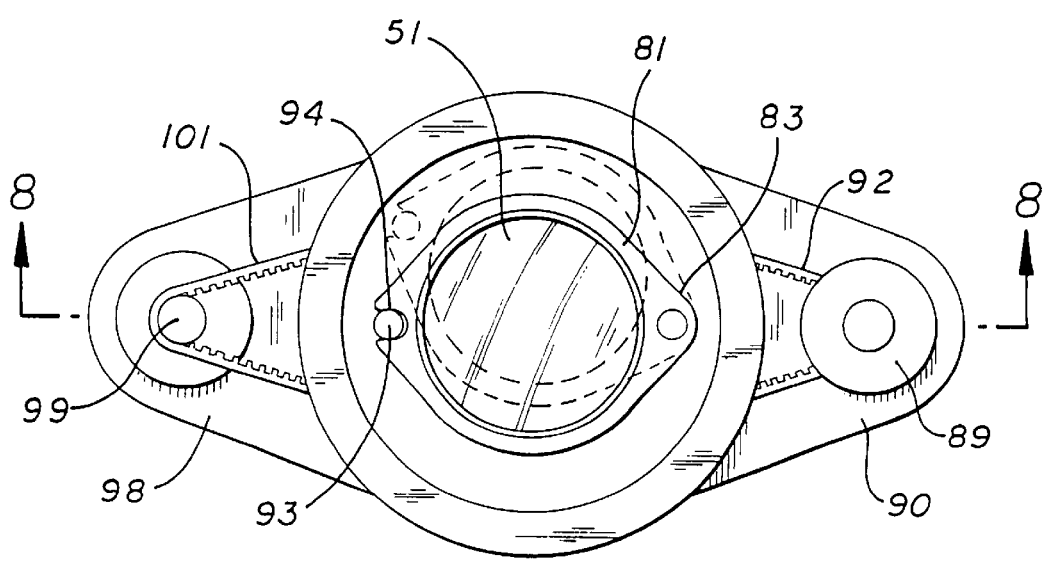
FIG. 7 is a top plan view of the image offset control unit of the invention, with the top annular portion removed.
Figure 8:
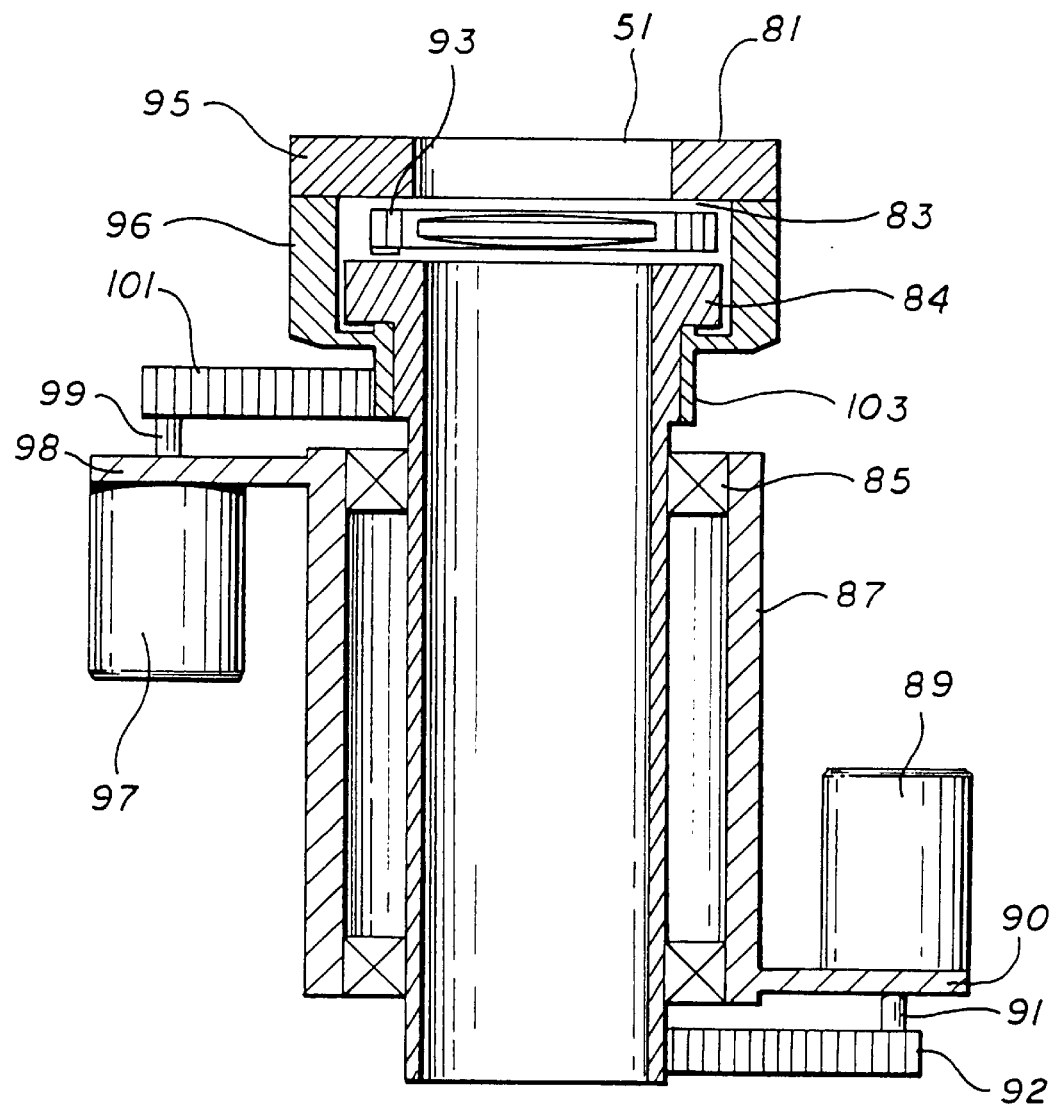
FIG. 8 is a side sectional view taken along lines 8—8 of FIG. 7.

FIGS. 7 and 8 illustrate the image offset control unit 80. As seen in these Figs., imaging lens 51 is contained in a fixture 81, which is mounted for pivotal motion about a first pivot post 83. Post 83 is carried by a first mounting member 84, which in turn is mounted by means of bearings 85 (or other suitable mounting mechanisms) for rotation about the longitudinal axis of member 84. Bearings 85 are mounted in the internal recess of a fixture housing 87. A first drive motor 89 is mounted on a flange portion 90 of housing 87 and has an output shaft 91 for driving a first drive belt 92 which is coupled to the lower portion of member 84. A second pivot post 93 is received in a second pivot aperture 94 formed in fixture 81. Second post 93 is secured to an annular upper portion 95 of a second rotatable member 96. A second drive motor 97 is mounted on a second flange portion 98 of fixture housing 87 and has an output shaft 99 for driving a second drive belt 101. Second drive belt 101 is arranged in driving engagement with the lower collar portion 103 of member 96.

In operation, when member 84 is driven by motor 89 and belt 92, the lens housing 81 pivots about post 93. Similarly, when outer member 96 is driven by motor 97 and belt 101, housing 81 is pivoted about post 83. This latter motion is suggested in FIG. 7, in which two different positions of the housing 81 are illustrated: one in full lines and the other in broken lines. By operating motors 89, 97 simultaneously, compound motion of the housing 81 in a plane about both pivot posts 83, 93 can be effected so that both translational and rotational motion can be imparted to the lens 51. Motors 89 and 97 are driven by the on-board computer 21, which is in turn driven by the p.c. workstation 10. By properly programming workstation 10, the desired motion can be imparted to imaging lens 51 in order to scan the aperture image over the desired ablation region of the corneal surface.

The invention offers the advantage of relatively wide area coverage without requiring a laser beam of size approximately equal to the treatment area. As a consequence, for hyperopic error corrections the transition zone can be fully formed using a controlled laser beam having a beam area substantially smaller than those required in prior art systems. This is highly advantageous since it requires substantially less energy than a larger beam generating laser, and avoids premature failure of optical components which are subject to deterioration due to high energy levels. The laser beam size should be large enough to cover the largest variable aperture required to effect the desired ablation. The maximum variable aperture contemplated with the slit/iris aperture has a largest dimension of approximately one half the largest treatment area. For most human eyes, this largest treatment area is approximately 10 mm. Consequently, a laser having a beam diameter of about 5 mm will provide regular ablations according to the invention. In the preferred embodiment the laser has a beam with a 6 mm maximum width. Further, the invention can be implemented in existing laser surgery systems by merely modifying the delivery system optics to enable the imaging lens 51 to be offset from the beam axis by selected amounts and to rotate with variable width slit/variable diameter iris arrangement. The design and construction of such modifications will be readily apparent to those of ordinary skill in the art of optomechanical design. Further, other types of corrections than hyperopic corrections can be effected by properly programming computer 21 to adjust the slit width and aperture radius.

The invention affords great flexibility in performing various types of corrections by virtue of the fact that the system can be programmed to accommodate patients having differently sized physical eye parameters and refractive correction requirements. The variable slit width/variable diameter iris arrangement is particularly adaptable for use in the treatment of hyperopia, hyperopic astigmatism and irregular refractive aberrations. For simultaneous treatment of hyperopia and hyperopic astigmatism, the ablation geometry is solved as a function of radial displacement and angular position of the aperture image about the rotational center. Further, in all procedures requiring a smoothing of the transition zone at the periphery of the ablation zone, the diameter of the iris is varied over a predetermined range along with the slit width variation. For refractive aberrations, a device such as a spatially resolved refractometer or a topography machine or both may be used to map the irregular surface contour of the cornea to determine the exact surface corrections required. Thereafter, the slit width and the iris diameter can be programmed such that corneal sculpting will achieve the desired spherical surface geometry.

In addition to hyperopic corrections, the invention can be used for other visual error corrections, both regular and irregular, for phototherapeutic keratectomy (typically used to ablate scar tissue), and for smoothing ablations. For example, to produce toric ablations according to the invention, a variable diameter circular aperture is scanned in an elliptical or other pattern of various sizes to create a smooth toric ablation. Such an ablation may contain a transition zone at the edge of the optical zone. By employing the invention, a much larger ablation zone is available than with conventional devices using variable apertures. As an example, for patients with equal sphere and cylinder (compound myopic astigmatism), a laser with a maximum treatment diameter of six millimeters will produce a toric ablation with a maximum minor axis value of 4.25 mm. An analogous ablation made with the eccentric rotating technique of the invention and a variable diameter iris using the same laser beam can produce a toric ablation with major and minor axes of 8.5 mm and 6.0 mm, respectively. As will be apparent to those skilled in the art, this provides much better coverage over the patient's pupil. In addition, the larger ablation is more likely to provide greater refractive stability than the smaller ablation.

To perform cylindrical ablations according to the invention, the iris diaphragm is set to a maximum value, and the eccentric lens is used to scan an ablated cylinder in periodic motion along the cylinder axis to produce longer cylindrical ablations. This negates the need to close the iris diaphragm while the laser is pulsed. Adjacent material may also be ablated on the ends of the cylinder so as to further extend the transition zone from the optical zone.

For phototherapeutic keratectomy applications, a scar which occurs centrally over the cornea can be ablated with the excimer laser by ablating a large area with a transition zone at the edge. As in the case with astigmatism and hyperopia, it is desirable to position the transition zone as far from the optically used portion of the cornea as possible. This avoids potentially undesirable side effects of scar removal, such as hyperopic shift in which changes in the curvature of the cornea create a hyperopic condition. In the past, a circular aperture has typically been imaged to approximately 6 mm diameter, and then opened or closed slightly while the laser fires a predetermined number of pulses to effect a transition zone and ablate the central scar. With the eccentric technique, it is possible to move the transition zone further outward by slightly displacing the image of the aperture between pulses. In addition, with the aperture closed further it can be scanned in a rotational pattern over the transition zone while the laser pulses to further ablate a transition zone which is much broader than would otherwise be possible to ablate.

The invention may also be used to treat irregular astigmatism to provide appropriate contour sculpting to effect correction of visual errors which cannot be fully corrected with eyeglasses (which only correct for sphere and cylinder). Since the geometry ablated according to the invention is not constrained to simple spherical and cylindrical geometries, irregular astigmatism can be treated in an especially effective manner. For example, a patient may have a corneal geometry which departs from spherical by conical rather than cylindrical geometry. In such a case, the cylinder blades are aligned similarly to the treatment of astigmatism. However, the combined motion of the eccentric lens and the cylinder blades will be such that one end of the image of the cylinder blade pair will be constant on the cornea, while the other end will be variably displaced during the ablation along an arc transverse to the cylinder axis. This technique can be extended to the use of elliptical ablations, resulting in ablations which would appear as distorted ovals rather than ellipses.

Lastly, the invention may be used to smooth ablations by displacing the rotational center of the profiled beam in a random or pseudo-random pattern so that beam defects are averaged over a much larger area. For example, a myopic ablation can be smoothed by scanning the iris diaphragm in a circular pattern as the iris diaphragm closes. This can produce a transition zone with gentle taper from the untreated area to the optical zone. Both the radial offset of the eccentric lens and the size of the iris diaphragm are varied during the treatment to produce a series of overlapping circular ablations of varying diameter and varying offset about the intended ablation center.

For any of the above specific correction procedures, a treatment table is normally constructed containing the value of all of the discrete radial and angular positions of the optomechanical elements used to scan the image over the relevant portion of the anterior corneal surface, as well as the number of laser pulses per position. A typical treatment table contains on the order of about 500 different entries. A sample of a one Diopter hyperopic treatment table is shown in appendix I. As noted above, it is preferable to reposition the ablation pattern significantly between successive pulses in order to minimize tissue heating. However, electromechanical elements such as iris motor 23, astigmatism motor 25, astigmatism angle motor 26 and the elements contained in the image offset control unit 80 all require finite minimum time periods to reposition the image. In addition, sudden motion of a mechanical element from one extreme position to the other can result in excessive and premature mechanical wear on the elements, necessitating frequent repair or replacement. In order to optimize a given ablation procedure so that the treatment is carried out within a minimum time period consistent with mechanical response times, the treatment table is sorted by the computer work station 10 to optimize the motion of the mechanical elements. The sorting process is done on the basis of both angular position and radial position, and a best fit approach is used to determine the angular and radial stepping sequences. In addition, the treatment table is also sorted into radial bands and the required angular positions within each band are established. The optomechanical elements are then driven in accordance with the sorted treatment table to carry out the procedure one band at a time. For example, the first band selected for ablation may be the outermost annular band, followed by the next inner band and continuing until the central band is completed. By separating the overall treatment into bands, motion of the mechanical elements within each particular band can be optimized. Also, in the event of an interruption in the treatment before completion, the patient will be left with a partially completed ablation pattern which will be easier to align when the procedure is resumed or which is optically beneficial if the procedure cannot be resumed.

The treatment table for a given procedure may incorporate special features designed to improve the efficiency of the procedure. For example, for some procedures (e.g., hyperopic correction) it can be beneficial to leave a small zone centered on the optical zone untreated. This can be done by constraining motion of the inner cylinder blade to guarantee occlusion in the small zone of interest. Further, compensation for variable or differential healing rates and for differential ablation depth due to tissue hydration may be factored into the treatment table. Also, standard tables can be constructed for a specific procedure—e.g., myopic correction—to different Dioptric correction values, and these standard tables can be sorted and combined to perform multiple repetitions of one or more standard tables to effect a given Dioptric correction. For example, standard tables may be created for a myopic correction for values of ¼, ½ and 1 Diopter. Using these tables, a 3.75 Diopter correction would proceed by performing the standard 1 Diopter correction three times, followed by the ½ Diopter correction and the ¼ Diopter correction.

While the invention has been described above with specific reference to ablation of the anterior corneal surface, other portions of the cornea may also be treated using the invention. For example, the epithelium may be mechanically removed by scraping, as is typically done in photorefractive keratectomy, and the exposed surface may be ablated. Further, the invention can also be used for laser keratomileusis of corneal lamella removed from the cornea. This procedure is described in U.S. Pat. No. 4,903,695 issued Feb. 27, 1990 for "Method and Apparatus For Performing A Keratomileusis Or The Like Operation". In applying the invention to this procedure, a flap of corneal tissue is physically removed from the cornea, the size of the removed portion typically lying in the range from about 8 to 10 mm wide and a variable thickness up to 400 microns. This flap of tissue is typically removed using a microkeratome. Next, the flap is placed in a suitable fixture—typically an element having a concave surface—with the anterior surface face down. Thereafter, the required ablation is performed on the reverse exposed surface of the flap, after which the ablated flap is repositioned on the cornea and reattached by suturing. Alternatively, after the flap is removed from the cornea, the exposed stromal tissue of the eye can be ablated according to the invention, after which the flap is re-attached over the freshly ablated stromal tissue.

While the above provides a full and complete disclosure of the preferred embodiments of the invention, various modifications, alternate constructions and equivalents may be employed as desired. For example, while the invention has been described with specific reference to the system of FIGS. 1 and 2, other systems may be employed, as desired. Further, lasers of other appropriate wavelengths than laser 28 may be used, if desired and effective. Also, laser beam systems which operate on the principle of thermal ablations, such as lasers having wavelengths lying in the infrared portion of the electromagnetic spectrum, may be used to implement the invention. In addition, while the radial and angular positioning of the profiled beam is accomplished with imaging lens 51 in the preferred embodiment, other optical scanning elements—such as rotating mirrors and prisms—may be employed, if desired. Therefore, the above description and illustrations should not be construed as limiting the invention, which is defined by the appended claims.

What is claimed is:

1. A method of performing selective ablation of a cornea of an eye to effect a refractive correction, said method comprising the steps of:
    (a) directing a laser beam toward the cornea;
    (b) creating a treatment table containing a listing of coordinate references for the beam to effect the desired refractive correction, the coordinate references specifying a plurality of different beam axis positions;
    (c) sorting the listing of coordinate references from the treatment table to generate a sculpting pattern which is substantially radially symmetric while said refractive correction is only partially complete; and
    (d) scanning the profiled beam over the corneal surface according to said sorted treatment table to produce said refractive correction.

2. The invention of claim 1 wherein said step (b) of creating a treatment table comprises generating a number of pulses at each coordinate reference to effect said refractive correction.

3. The invention of claim 1, wherein the step (b) of creating the treatment table includes compensating for differential ablation depth.

4. The invention of claim 1, further comprising separating said refractive correction into a plurality of partial corrections and sequentially performing the partial corrections.

5. An ophthalmological surgery system for performing selective ablation of a corneal surface of an eye to effect a desired corneal shape, said system comprising:
    means for directing a laser beam along a path;
    variable aperture means for profiling said beam to produce a variable area profiled beam; and
    means for scanning the profiled beam over a predetermined area of the corneal surface, wherein scanning comprises ablating at a series of beam axis locations in the predetermined area, a plurality of the locations specified by a different coordinate reference while varying the profile of the beam, and wherein scanning is performed according to a sorted treatment table which includes a listing of coordinate references and a variable aperture configuration at each coordinate reference, the table sorted to define a series of radially symmetric partial treatments.

6. The invention of claim 5, wherein the scanning means comprises at least one member of the group consisting of a lens, a mirror, and a prism.

7. The invention of claim 5, further comprising a controller coupled to the variable aperture profiling means and the scanning means, the controller comprising the sorted treatment table.

8. The invention of claim 7, wherein the table further comprises a listing of the number of coordinate pulses at each coordinate reference to effect the desired corneal shape.

9. A method of performing selective ablation of a corneal surface of an eye to effect a desired corneal shape, said method comprising the steps of:
    (a) directing a laser beam having a beam axis toward a variable aperture;
    (b) profiling the beam with the variable aperture to produce a variable area profiled beam;
    (c) creating a treatment table identifying a listing of values including coordinate references for the axis of the profiled beam, a variable aperture configuration at each coordinate reference, and a number of pulses at each coordinate reference to effect the desired corneal shape;

(d) sorting the listings in the treatment table to a sorted treatment table of the profiled beam, the sorted treatment table defining a series of radially symmetric partial treatments; and (e) scanning the profiled beam by moving the beam axis over a predetermined treatment area of a corneal surface while varying the profile according to the sorted treatment table.

10. The invention of claim 1, wherein the variable aperture comprises a variable width slit, and wherein said step (e) of scanning includes a step of rotating the variable width slit.

11. A method of performing selective ablation of a corneal surface of an eye to effect a predetermined myopic refractive correction, said method comprising the steps of:

(a) directing a laser beam having a beam axis toward a variable aperture;

(b) profiling the beam with the variable aperture to produce a variable area profiled beam;

(c) creating a treatment table identifying a listing of values including coordinate references for the axis of the profiled beam, a variable aperture configuration at each coordinate reference, and a number of pulses at each coordinate reference to effect the desired corneal shape;

(d) sorting the listings in the treatment table to a sorted treatment table of the profiled beam, the sorted treatment table defining a series of radially symmetric partial treatments; and (e) scanning the profiled beam by moving the beam axis over a predetermined area of a corneal surface while varying the size of the aperture according to the sorted treatment table to produce said myopic refractive correction.

12. The method of claim 11 wherein said step (e) of scanning is performed by scanning the profiled beam over a predetermined position of the corneal surface while enlarging the size of the variable aperture.

13. The method of claim 11 wherein said step (e) of scanning is performed by scanning the profiled beam over a predetermined position of the corneal surface while reducing the size of the variable aperture.

14. The method of claim 11 wherein said step (e) of scanning is performed by establishing an axis of rotation for the profiled beam at a predetermined position on the corneal surface and scanning the profiled beam about the predetermined position by varying a displacement of the profiled beam from the axis of rotation and by varying an angular position of the profiled beam about the axis of rotation in a preselected manner.

15. A method of performing selective ablation of a corneal surface of an eye to effect a desired corneal shape, said method comprising the steps of:

(a) directing a laser beam toward a variable aperture comprising a variable width slit and a variable diameter diaphragm;

(b) profiling the beam with the variable aperture to produce a variable area profiled beam;

(c) creating a treatment table identifying a listing of values including coordinate references for the profiled beam, a variable aperture configuration at each coordinate reference, and a number of pulses at each coordinate reference to effect the desired corneal shape;

(d) sorting the listings in the treatment table to a sorted treatment table of the profiled beam, the sorted treatment table defining a series of radially symmetric partial treatments; and (e) scanning the profiled beam over a predetermined treatment area of a corneal surface while varying the profile according to the sorted treatment table, wherein scanning includes a step of selectively varying the width of the slit and a step of selectively varying the diameter of the diaphragm.

16. The method of claim 15, wherein said step (e) of scanning includes a step of rotating the variable width slit.

17. The method of claim 15, wherein at least some of the values include compensation for differential ablation depth.

18. The method of claim 15, wherein the step (b) of profiling the beam produces an elongate substantially rectangular beam shape having first and second opposed sides defined by the variable width slit and first and second rounded ends defined by the variable diameter diaphragm.

19. A method of performing selective ablation of a corneal surface of an eye to effect a desired corneal shape, said method comprising the steps of:

(a) directing a laser beam toward a variable aperture comprising a variable width slit and a variable diameter diaphragm;

(b) profiling the beam with the variable aperture to produce a variable area profiled beam, wherein profiling the beam produces an elongate substantially rectangular beam shape having first and second opposed sides defined by the variable width slit and first and second rounded ends defined by the variable diameter diaphragm;

(c) creating a treatment table identifying a listing of values including coordinate references for the profiled beam, a variable aperture configuration at each coordinate reference, and a number of pulses at each coordinate reference to effect the desired corneal shape;

(d) sorting the listings in the treatment table to a sorted treatment table of the profiled beam, the sorted treatment table defining a series of radially symmetric partial treatments; and (e) scanning the profiled beam over a predetermined treatment area of a corneal surface while varying the profile according to the sorted treatment table, wherein scanning includes a step of selectively varying the width of the slit and a step of selectively varying the diameter of the diaphragm.

20. A method of performing selective ablation of a corneal surface of an eye to effect a desired corneal resculpting, said method comprising the steps of:

directing a laser beam toward the cornea along a beam path;

establishing a center of rotation for the beam;

displacing said beam path from the center of rotation by a displacement, wherein the beam has an elongate substantially rectangular beam shape, and wherein the displacing step is performed so that the elongate substantially rectangular beam shape is oriented laterally relative to the center of rotation;

varying the displacement of said beam from the center of rotation; and varying an angular position of said beam about the center of rotation and rotating the elongate substantially rectangular beam shape so that the rotated elongate substantially rectangular beam shape is laterally oriented relative to the center of rotation;

intercepting the beam with a variable diameter iris and a variable width slit; and varying a diameter of the iris and a width of the slit.

21. A method of performing selective ablation of a corneal surface of an eye to effect a desired corneal resculpting, said method comprising the steps of:

directing a laser beam toward the cornea along a beam path;

establishing a center of rotation for the beam;

displacing said beam path from the center of rotation by a displacement, wherein the beam has an elongate substantially rectangular beam shape, and wherein the displacing step is performed so that the elongate substantially rectangular beam shape is oriented laterally relative to the center of rotation;

varying the displacement of said beam from the center of rotation;

varying an angular position of said beam about the center of rotation and rotating the elongate substantially rectangular beam shape so that the rotated elongate substantially rectangular beam shape is laterally oriented relative to the center of rotation; and rotating the variable width slit in coordination with the varying of the angular position of the beam, the slit having a first edge movable relative to an opposed second edge, wherein the slit rotating step is performed so that a first elongate side of the beam defined by the first edge of the slit comprises an inner edge oriented toward the axis of rotation and a second elongate side of the beam defined by the second edge of the slit comprises an outer edge oriented toward a peripheral boundary of said desired corneal resculpting.

* * * * *